(12) United States Patent
Kieturakis

(10) Patent No.: US 11,324,536 B2
(45) Date of Patent: May 10, 2022

(54) SEAL FOR LAPAROSCOPIC ACCESS PORT

(71) Applicant: Maciej J. Kieturakis, Los Altos Hills, CA (US)

(72) Inventor: Maciej J. Kieturakis, Los Altos Hills, CA (US)

(*) Notice: Subject to any disclaimer, the term of this patent is extended or adjusted under 35 U.S.C. 154(b) by 75 days.

(21) Appl. No.: 16/444,275

(22) Filed: Jun. 18, 2019

(65) Prior Publication Data

US 2019/0380743 A1 Dec. 19, 2019

Related U.S. Application Data

(60) Provisional application No. 62/687,088, filed on Jun. 19, 2018.

(51) Int. Cl.
*A61B 17/34* (2006.01)
*A61M 13/00* (2006.01)

(52) U.S. Cl.
CPC ...... *A61B 17/3462* (2013.01); *A61B 17/3423* (2013.01); *A61M 13/003* (2013.01); *A61B 2017/3466* (2013.01); *A61B 2017/3492* (2013.01)

(58) Field of Classification Search
CPC ............ A61B 17/3462; A61B 17/3423; A61B 2017/3466; A61B 2017/3492; A61B 2017/3429; A61B 17/3431; A61B 2017/347; A61M 13/003
See application file for complete search history.

(56) References Cited

U.S. PATENT DOCUMENTS

| | | | |
|---|---|---|---|
| 6,171,282 B1 * | 1/2001 | Ragsdale | A61B 17/3423 604/164.11 |
| 6,454,783 B1 | 9/2002 | Piskun | |
| 2009/0093752 A1 * | 4/2009 | Richard | A61B 17/3423 604/24 |
| 2011/0124970 A1 * | 5/2011 | Kleyman | A61B 17/3423 600/208 |
| 2011/0251464 A1 * | 10/2011 | Kleyman | A61B 17/3423 600/206 |
| 2011/0295074 A1 * | 12/2011 | Stefanchik | A61B 17/3423 600/201 |
| 2012/0095297 A1 | 4/2012 | Dang et al. | |
| 2012/0116362 A1 | 5/2012 | Kieturakis | |
| 2012/0157781 A1 * | 6/2012 | Kleyman | A61B 17/0218 600/208 |

(Continued)

OTHER PUBLICATIONS

International Search Report and Written Opinion for PCT/US2019/037903 dated Sep. 10, 2019.

*Primary Examiner* — Theodore J Stigell
(74) *Attorney, Agent, or Firm* — Wilson Sonsini Goodrich & Rosati

(57) ABSTRACT

A deformable seal for use together with a laparoscopic port has a deformable body with an upper region, a lower region, and a narrowed waist. A plurality of tool passing channels are individually formed in an axial direction through the deformable body, and each tool passing channel has a tool entrance on a surface of the upper region and a tool exit on a surface of the lower region. The tool passing channels are sufficiently elastic to conform to and seal about a shaft of a laparoscopic tool present in the channel and to close to inhibit leakage of an insufflation gases when the tool is removed from the tool passing channel.

13 Claims, 12 Drawing Sheets

(56) References Cited

U.S. PATENT DOCUMENTS

| | | |
|---|---|---|
| 2012/0190933 A1 | 7/2012 | Kleyman |
| 2012/0245428 A1 | 9/2012 | Smith et al. |
| 2013/0253279 A1* | 9/2013 | Smith ................ A61B 17/0218 600/204 |
| 2016/0081752 A1* | 3/2016 | Kieturakis ............. A61B 34/70 606/130 |

* cited by examiner

SEAL FOR LAPAROSCOPIC ACCESS PORT

CROSS-REFERENCE TO RELATED APPLICATION

This application claims the benefit of and priority from Provisional Patent Application No. 62/687,088, filed on Jun. 19, 2018, the full disclosure of which is incorporated herein by reference.

BACKGROUND OF THE INVENTION

1. Field of the Invention

The present invention relates generally to medical systems, tools, and methods. More particularly, the present invention relates to systems and tools for laparoscopic access, typically for access of multiple laparoscopic tools through a single incision or the umbilicus.

In recent years, many open surgical procedures performed in the abdominal cavity have been replaced by minimally invasive procedures performed through several very small incisions using an endoscope, referred to as a laparoscope, inserted through one of the incisions. The other incisions are used for introducing surgical tools, and the abdominal cavity is inflated to create a space for performing the surgery. Such procedures are commonly called "laparoscopic", and can be used for gallbladder removal, hernia repair, hysterectomy, appendectomy, gastric fundoplication, and other procedures. Similar endoscopic, thoracoscopic and other procedures are performed in other body cavities without inflation.

While a great advance over open surgical procedures, which often require an incision of several inches or more through the abdominal wall, such laparoscopic procedures still require smaller incisions through muscle or fascia in several separate sites. Each incision increases the risk of infection, bleeding trocar site herniation, increased postoperative pain, compromised cosmetic result, and other adverse patient outcomes.

As an improvement over such laparoscopic procedures, "single port" laparoscopy has been proposed where a single access port is inserted through the umbilicus (the patient's navel). Access solely through the umbilicus is advantageous since it provides a superior cosmetic and functional result and lessens other risks of the procedure related to multiple port placements. Introducing the laparoscope and all other tools necessary for the surgery through a single port, however, makes performance of the procedures more difficult. In particular, the use of conventional laparoscopic tools, which are typically straight, makes it difficult to approach a single target area in the treated tissue with two or more tools at the same time.

Further improvements in the field of single port laparoscopic surgery are described in U.S. Patent Publications 2012/0116362 and 2016/0081752, commonly assigned with the present application, the full disclosures of which are incorporated herein by reference. As generally described in these applications, systems for performing single port laparoscopic procedures include a transcutaneous seal and a plurality of tools. The tools comprise a substantially rigid tubular seal having a core which is translatably and rotatably disposed in the sleeve. The handle at the proximal end of the tool controls an end effector at the distal end of the tool. The sleeves of the tools are locked in the transcutaneous seals so that they remain in a fixed geometric relationship which prevents the tools from interfering with each other during laparoscopic procedures. Adjacent tools are held by a pivot structure in US2012/0116362 and by an external frame in US2016/0081752.

While representing significant advances in the art, the systems and protocols described in 2012/0116362 and 2016/0081752 do not always provide complete sealing of the access port while allowing convenient introduction, removal, and exchange of laparoscopic tools during a procedure.

Thus, it would be a benefit to provide further improved systems and tools for laparoscopic access through single and individual ports for performing minimally invasive robotic surgical procedures. It would be particularly desirable to provide improved laparoscopic ports and seals which afford complete sealing of the access port while allowing convenient introduction, removal, and exchange of laparoscopic tools during a procedure. At least some of these objectives will be met by the inventions described hereinafter.

2. Description of the Background Art

U.S. Patent Publications 2012/0116362 and 2016/0081752 have been described above. U.S. Pat. No. 6,454,783 describes port structures intended for access through the umbilicus.

SUMMARY OF THE INVENTION

In a first aspect of the present invention, a deformable seal for a laparoscopic port comprises a deformable body having an upper region, a lower region, and a narrowed waist between the upper and lower regions. A plurality of tool passing channels are formed axially (where the axis is aligned top to bottom of the seal) through the deformable body, where each tool passing channel has a tool entrance on an upper surface of the upper region and a tool exit on a lower surface of the lower region. Each of the tool passing channels is typically configured to be sufficiently elastic to conform to and seal against and about a shaft of a laparoscopic tool removably inserted in the channel so that a surrounding surface of the channel will close or collapse about a circumference of the shaft to inhibit leakage of an insufflation gas as the tool is inserted through the tool passing channel of the seal and after the tool has been removed from the tool passing channel.

In specific embodiments of the deformable seals of the present invention, an insufflation channel may also be formed axially through the deformable body, typically having an insufflation tube connector attached to the upper surface of the upper region and an insufflation tube exit on a surface of the lower region. In this way, the insufflation of the patient may be maintained through a single laparoscopic port, eliminating the need to form a separate incision to insert an insufflation needle or port.

In further exemplary embodiments, the upper region of the seal will be larger than the lower region, and in particular will have a larger surface area allowing the tool entry points to be spaced further apart. The deformable body will be specifically configured to be deformed while the seal is passed through an aperture in the laparoscopic port, allowing the narrowed waist of the seal to seat in and hermetically seal against the aperture to inhibit insufflation loss through the aperture.

Typically at least some of the plurality of tool passing channels will have an arcuate or otherwise curved configuration in order to receive laparoscopic tools having an arcuate midsection. In other specific instances, the tool entrances on the upper surface may have valves such as split membrane valves; in order to still further inhibit insufflation loss. Additionally or alternatively, such valves could be formed over the tool exits in the bottom surface of the lower region of the deformable seal. Others of the tool passing channels, however, may be straight particularly when intended to receive a laparoscope having a straight shaft.

In a preferred aspect of the present invention, the deformable body will have an insertion channel formed laterally (in a side-to-side direction orthogonal to the axial direction) across the lower region thereof. An insertion tool will be provided and be configured to be introduced into the insertion channel such that the tool can be manually advanced to push and to deform the lower region of the deformable body in order to allow the lower region to pass through the aperture of the laparoscopic port and to self expand on the other side of the port with the narrowed waist region seating in the aperture.

Usually, the insertion channel will comprise a sheath or other lining formed thereabout in order to protect the seal from damage as the insertion tool is inserted into the insertion channel. Typically, the sheath lining the insertion channel will be flexible to allow elongation and often the curved or in a serpentine pattern when the deformable seal is free from constraint and the insertion tool is not in the insertion channel. Thus, insertion of a straight insertion tool will straighten and elongate the insertion channel which in turn narrows the profile of the lower region of the deformable seal in order to facilitate introduction through the aperture of the laparoscopic port.

In still further instances, the lower region region will have a nose or other protrusion extending from one side in a lateral direction where the insertion channel extends across the lower region and into the nose or other protrusion. The nose profile can be smaller than the remainder of the lower region, thus allowing a leading portion of the lower region (the nose) to be sufficiently small to pass through the aperture and facilitate introduction of the remaining lower region of the seal through the laparoscopic port.

In still further exemplary embodiments, a pull strap may be affixed to the deformable seal to facilitate removable of the seal after it has been introduced into the laparoscopic port. For example, the pull strap may be affixed at one end to the sheath in the lower portion of the deformable seal and at another end to the upper region of the deformable seal. A pull strap can then be pulled to facilitate deformation and removal of the deformable seal, particularly the lower region thereof, from the laparoscopic port.

In additional exemplary embodiments, the deformable body may comprise a flexible shell filled with a deformable or malleable filler material. For example, the flexible shell may be a polymer, usually a non-distensible that can change shape but resist stretching and elongation as the deformable seal is introduced into the laparoscopic port. The filler material may be a gel, a particulate filler material (e.g., beads), a viscous liquid, or the like, in order to allow the body to deform while it is being introduced to and removed from the laparoscopic port.

In still further exemplary embodiments, the tool passing channels may be lined with a protective material or structure. For example, the tool passing channels may be lined with elongate elements, such as skis or skids which serve as protective barriers as a laparoscopic tool is advanced through the tool passing channel. Alternatively, the protective elements may be spotted pavers or other discrete elements which also act to inhibit damage to the shell of the deformable body as laparoscopic tools are introduced through the tool passing channels.

In a second aspect of the present invention, a laparoscopic port system comprises a deformable seal according to any of the embodiments as described above. The systems further include a laparoscopic port having an aperture for placement over a percutaneous incision, typically through an umbilicus, where the aperture is configured to receive the deformable seal so that the lower region passes through the percutaneous incision, the waist region is received within the aperture, and the upper region remains above the deformable seal in order to removably receive laparoscopic tools.

In some instances, the laparoscopic port which is part of the laparoscopic port system may comprise a frame having a periphery and a central opening (which defines the aperture) in a horizontal plane. A first tool holder is pivotally attached to an exterior of the frame at a first location, where the first tool holder is configured to removably receive a first tool having a curved mid-portion which passes through the tool passing channel of the deformable body when the deformable body is in aperture. A second tool holder may be pivotally attached to an exterior of the frame at a second location, where the second tool holder is also configured to removably receive a laparoscopic tool having a curved mid-portion which passes through the tool passing channel of the deformable body when the deformable body is in the aperture.

In still further specific aspects, the first and second tool holders may be configured to allow the tools to pivot in at least two vertical planes relative to the frame, usually where the mid-portions of the tools are positioned to avoid interference as the tools are pivoted in these at least two vertical planes.

In other instances, the port systems may further comprise an attachment sleeve configured to be placed through the central opening in the port as well as through the percutaneous incision accessing the body cavity. The attachment sleeve typically includes a lower ring or other structure which may be passed through the aperture and into the body cavity, and an upper ring or other element which may be rolled down in order to immobilize the a stabilizing plate of the port on or over the incision. An inner passage through attachment sleeve acts as the aperture for receiving the laparoscopic seal as described elsewhere herein.

In still further aspects of the present invention, methods for performing laparoscopic surgery through a single port comprise securing a port having a central opening defining an aperture over an incision in a patient's abdomen to provide such "single port" access. A deformable body is introduced through the aperture, where a portion of the deformable body passes through the aperture and into the patient's abominable cavity, and an upper region of the seal remains above the aperture with a narrowed waist (disposed between the upper and lower regions) anchored or otherwise secured in a perimeter of the aperture. After the deformable body has been introduced, and the abdominal cavity insufflated, a first laparoscopic tool (or sometimes the laparoscope) may then be passed through a first tool passing channel in the seal so that the channel conforms to and seals against a shaft of the first tool. Similarly, a second laparoscopic tool may be passed through a second tool passing channel in the seal so that the second channel conforms to and seals against the second tool. Additional channels and tools may be provided within the scope of the present invention.

In preferred aspects of the methods herein, the lower region will be smaller than the upper region in order to facilitate passage of the lower region through the aperture in the laparoscopic port while maximizing the upper surface area for tool access. The narrowed waist will have dimensions selected to seat in the aperture and seal to the port. Often, at least some of the plurality of tool passing channels will have an arcuate or other curved shape configured to receive a similarly shaped laparoscopic tool.

In still further specific instances of the methods of the present invention, the laparoscopic tools may have valves formed over at least some of the tool entrances on the surfaces of the upper region. Introducing the deformable body through the aperture may comprise inserting and introducing tool into a channel formed laterally across the lower region of the deformable body. In this way, the tool can be manually advanced to push and deform the lower region of the deformable body so that the lower region can more easily pass through the aperture and self expand on the other side of the port in order to anchor the narrowed waist of the deformable body in the aperture. After the procedure is completed, the deformable port may be removed from the aperture, typically by pulling on a pull strap affixed to the lower region.

After the deformable seal has been placed in the laparoscopic port, as described above, a laparoscopic procedure may be performed by attaching a first tool to a first pivotal attachment element on a first location on an outer peripheral of the port. A second tool may similarly be attached to a second pivotal attachment element at a second location on an outer peripheral of the frame. Each tool has distal and proximal sections which lie on axis's passing through the pivotal attachment elements in mid-portions which remain positioned within the tool passing channels of the seal. Tools may then be manipulated by a user during surgery, where the combination of the pivotal attachments and the flexible tool passing channels help the tools avoid interference as the tools are manipulated during the surgery.

In still further embodiments, additional third, fourth, and even more tools may be attached to the laparoscopic port and then introduced through tool passing channels in the deformable seal. Additionally, one, two, three or more of previously introduced laparoscopic tools may be removed from the tool passing channels and detached from the laparoscopic port as a procedure progresses. The detached tools may be replaced by alternative tools as the procedure progresses. During the procedures, the tools may be manipulated including extending and retracting proximal into the tools to extend and retract distal sections of the tool.

During the procedure, at most constricted portions of the incision (usually the fascia or the skin), the inner gel or other deformable filler of the seal is able to accommodate displacements caused by the inserted laparoscopic tools by shifting to the upper and/or lower regions of the deformable seal. Such displacement will allow all the tools to move freely within the smallest possible incision, which could surround the tools positioned against each other separated only by the thickness of a semi-elastic shell of the deformable seal.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
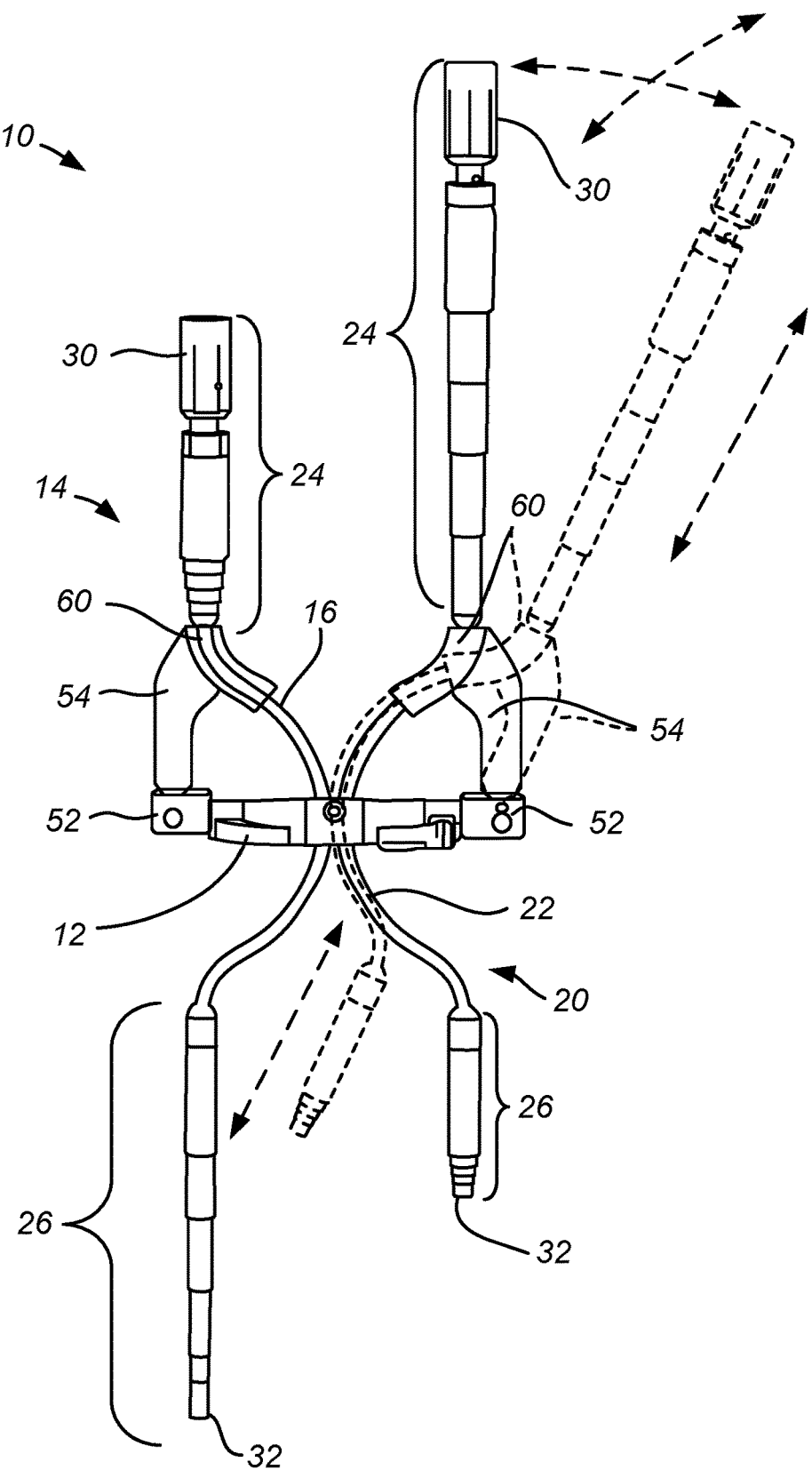
FIG. 1 illustrates a prior art access port having a pair of pivotally mounted laparoscopic tools intended for use in single port laparoscopic surgery as described in US 2016/0081752.
Figure 2:
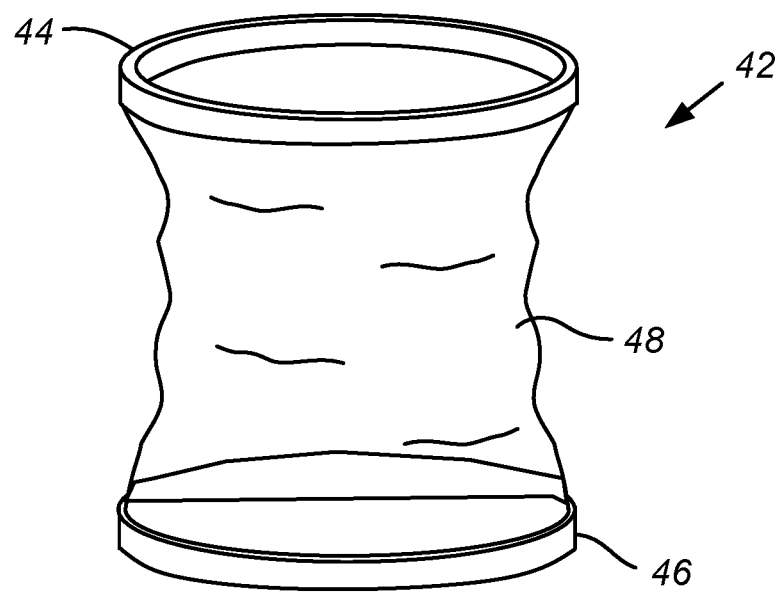
FIG. 2 illustrates a prior art transcutaneous seal intended for use in combination with the access port of FIG. 1 as described in US 2016/0081752.
Figure 3:
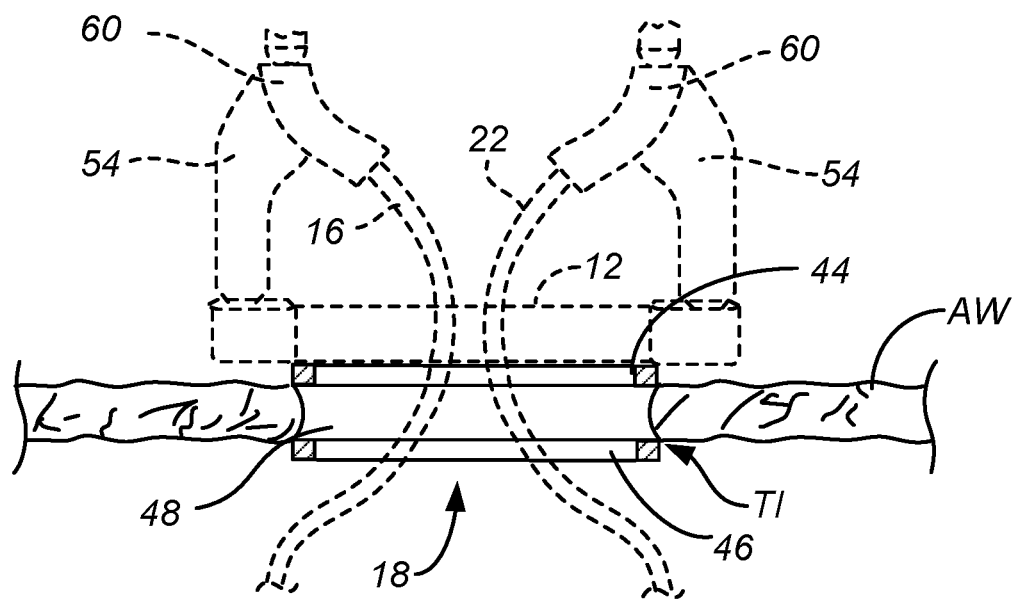
FIG. 3 illustrates the prior art transcutaneous seal of FIG. 2 mounted in the prior art access port of FIG. 1 as described in US 2016/0081752.

Referring now to FIGS. 1-3, a prior art laparoscopic tool system 10 of the type described in US2016/0081752, previously incorporated herein by reference, comprises a tool attachment frame 12 having a first tool 14 and a second tool 20 pivotally attached thereto. The first tool has a mid-portion 16 and the second tool has a mid-portion 22, and both mid-portions extend generally inwardly from an axis of the tool. Both mid-portions 16 and 22 are preferably circular and have a radius emanating from a virtual rotation point. The virtual rotation point is generally aligned with a pivoting assembly attached to an outer periphery of the tool attachment frame 12. Having the virtual rotation points of each tool located outside the periphery of the ring allows the generally circular mid portions 16 and 22 to pass and move through the central opening 18 of the frame 12 without interfering with each other. While the mid-portions 16 and 22 could alternatively have non-circular geometries which extend radially inward relative to the frame 12, for example being oval or polyhedral, the circular shape causes the passage point of the mid-portion to remain fixed within the central opening 18 of the frame so long as the tool is constrained to move in to orthogonal planes by the pivot attachment as will be explained in more detail hereinafter.

Referring now to FIG. 2, a prior art transcutaneous seal 42 comprises an upper end or ring 44 and a lower end or ring 46. A flexible sheath 48 extends between the upper and lower ends. The seal may be disposed in a transcutaneous incision TI through and abdominal wall AW, as shown in FIG. 3. Conveniently, the sheath 48 may be generally elastic, and the length of the sheath may be adjusted by rolling the sheath over either the upper or lower rings, allowing the transcutaneous seal to be stretched and placed over the transcutaneous insertion.

Referring now to FIG. 2, a prior art transcutaneous seal 42 comprises an upper for ring 44 and a lower end or ring 46. A flexible sheath 48 extends between the upper and lower ends. The seal may be disposed in a transcutaneous incision TI through and abdominal wall AW, as shown in FIG. 3. Conveniently, the sheath 48 may be generally elastic, and the length of the sheath may be adjusted by rolling the sheath over either the upper or lower rings, allowing the transcutaneous seal to be stretched and placed over the transcutaneous insertion.

As further shown in FIG. 3, once in place, the prior art tool attachment frame 12 may be attached to the upper end or ring 44 of the transcutaneous seal 42, thus fixing the frame in place relative to the patient. The tools 14 and 20 may then be attached to the vertical support arms 54 and the tools then used to perform a laparoscopic procedure by manipulating the proximal ends of the tools to reposition the distal ends where desired. As the procedure progresses, the tools may be interchanged for other tools by simply detaching the tool attachment blocks 60 from the vertical support arms 54.

Figure 4:
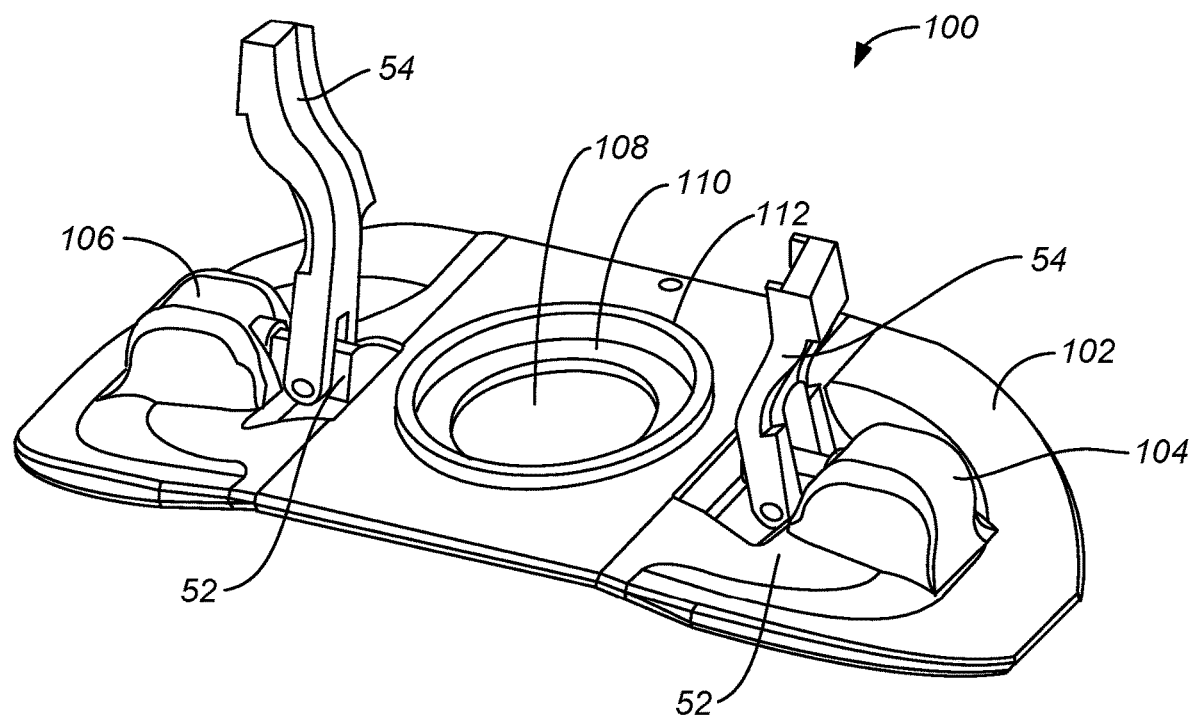
FIG. 4 is a perspective view of a laparoscopic access port having a pair of pivotally mounts configured to removably hold laparoscopic tools in accordance with the principles of the present invention.
Figure 5:
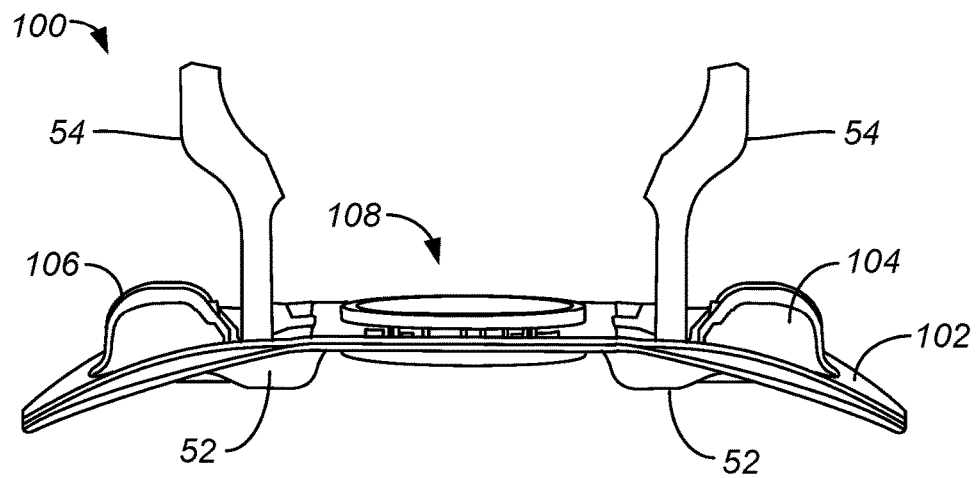
FIG. 5 is a front view of the laparoscopic access port of FIG. 4.

Referring now to FIGS. 4 and 5, a laparoscopic port 100 includes a deformable body 102 having a right post 104 and a left post 106 extending upwardly from an upper surface of the body. The deformable body has a generally arcuate profile, as best seen in FIG. 5, so that it may be placed over a patient's stomach so that a central aperture 108 can align with the patient's umbilicus. Central aperture 108 has a flange structure 110 surrounding an open central portion and a vertical wall 112 extending about the outer periphery of the flange. The deformable body will have arms 54 attached to pivots 52 generally as described above with respect to the U.S. Patent Publication 2016/0081752, the full disclosure of which has been incorporated herein by reference. It will be appreciate that these arms 54 are intended for attaching laparoscopic tools so that the tools may be introduced through the aperture 108, as described in detail in the incorporated patent publications.

Figure 6:
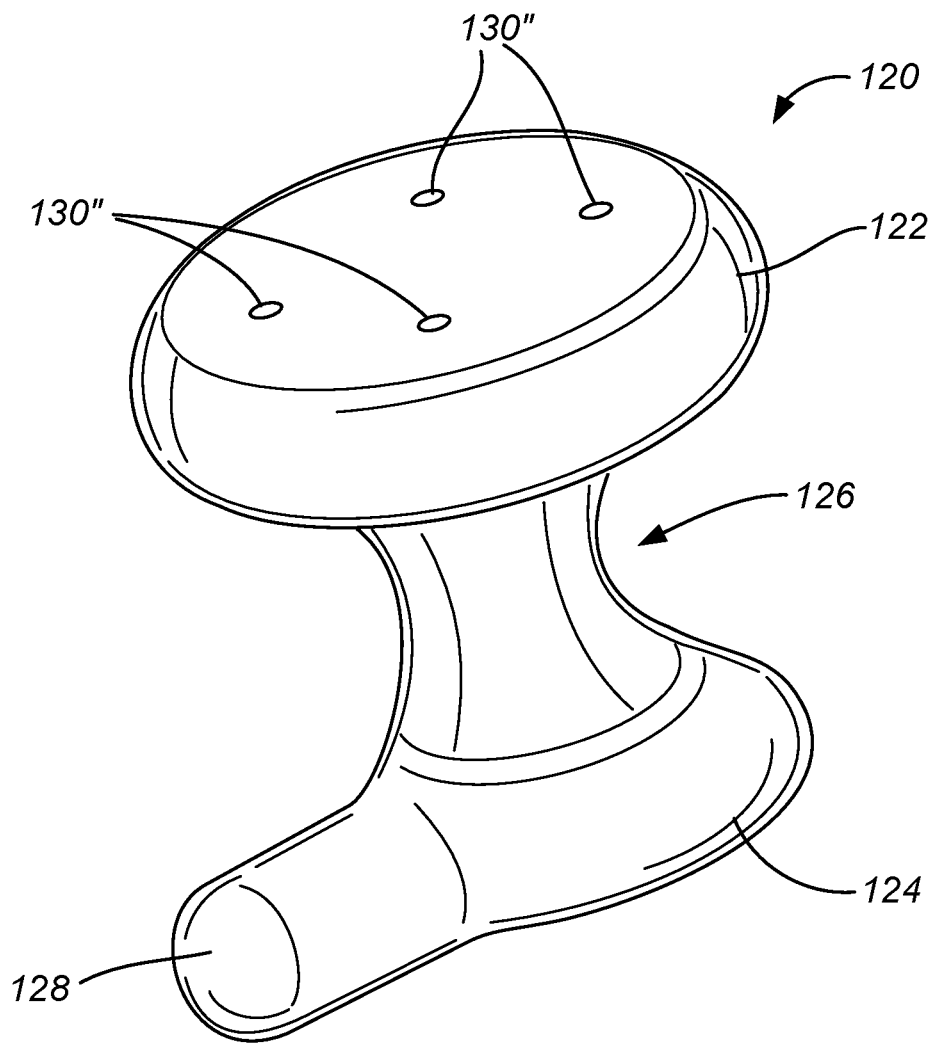
FIG. 6 illustrates an exemplary access port seal in accordance with the principles of the present invention.

Referring now to FIG. 6, a deformable seal 120 has an upper region 122 and a lower region 124. A narrowed waist region 126 is disposed between a lower surface of the upper region and an upper surface of the lower region. A nose or other protrusion 128 is formed to project laterally from one side of the lower region 124 where the nose serves to facilitate introduction of the deformable seal 120 through the central aperture 108 of the laparoscopic port 100, as described in greater detail below. Both the upper region 122 and the lower region 124 have generally circular cross-sections in a lateral plane and generally oval cross-sections in an axial or vertical plane. The narrowed waist region has a generally hour-glass shape, and the nose typically has a bullet shape, i.e. being generally cylindrical with a rounded distal tip. While these geometries are exemplary, other specific shapes could be used in other designs in accordance with the principles of the present invention.

Figure 7B:
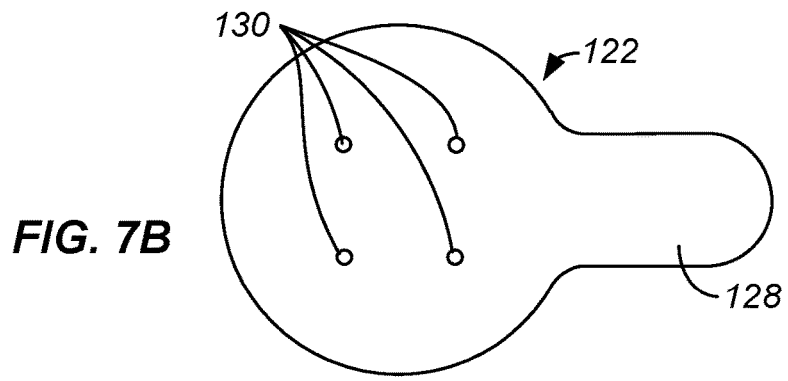
FIGS. 7A, 7B, and 7C, are front, bottom, and top views of the exemplary access port seal of FIG. 6.
Figure 7A:
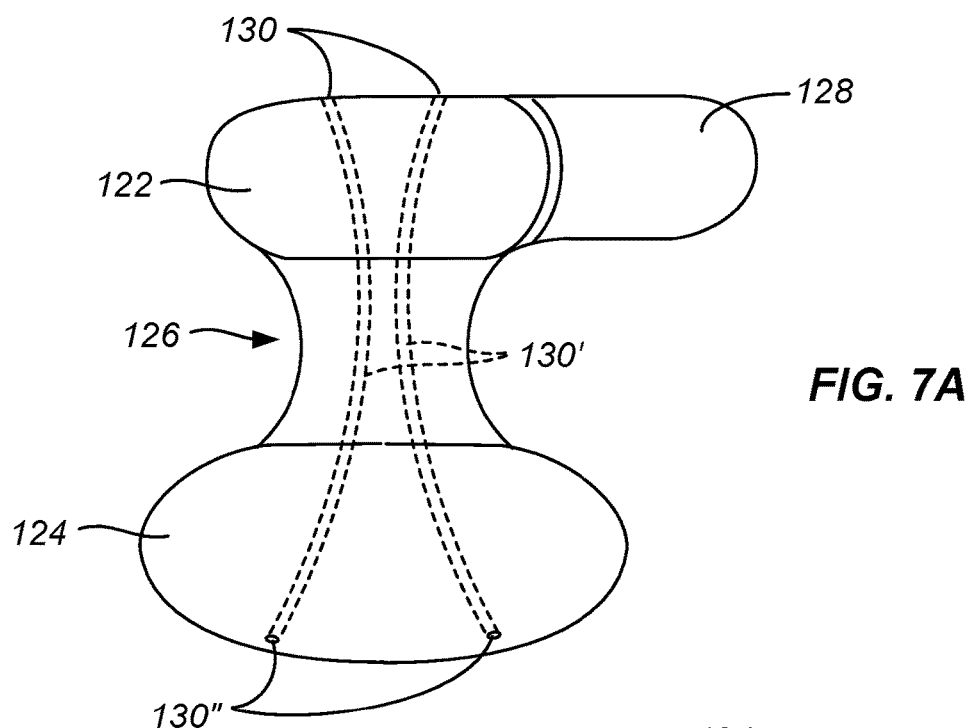
Figure 7C:
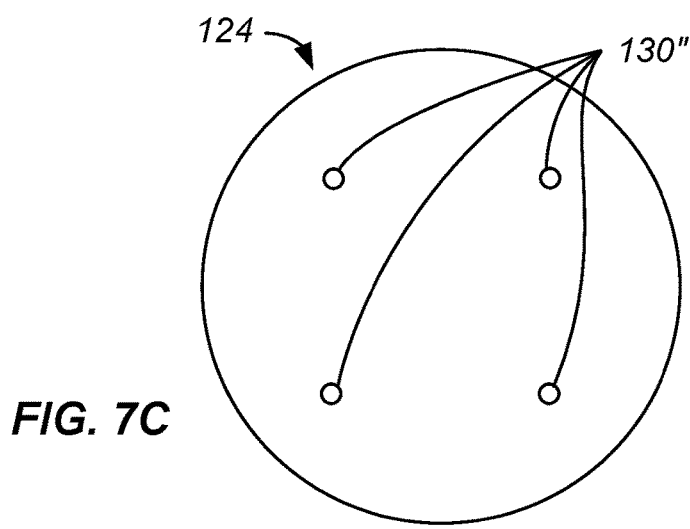

Referring now to FIGS. 7A through 7C, the deformable body 120 has a plurality of tool passing channels 130 formed axially (where the axis is aligned top to bottom of the seal) there through from an upper surface of the upper region 122 to a lower surface of the lower region 124. Upper openings are marked as 130, with the centrally aligned passages marked as 130', and the lower exit openings marked as 130". As described in more detail below, laparoscopic tools having curved mid-sections, such as though described in detail in U.S. Patent Publication Numbers 2012/00116362 and 2016/0081752, the full disclosures of which have been previously incorporated herein by reference, may be introduced through the passages 130'.

Figure 8A:
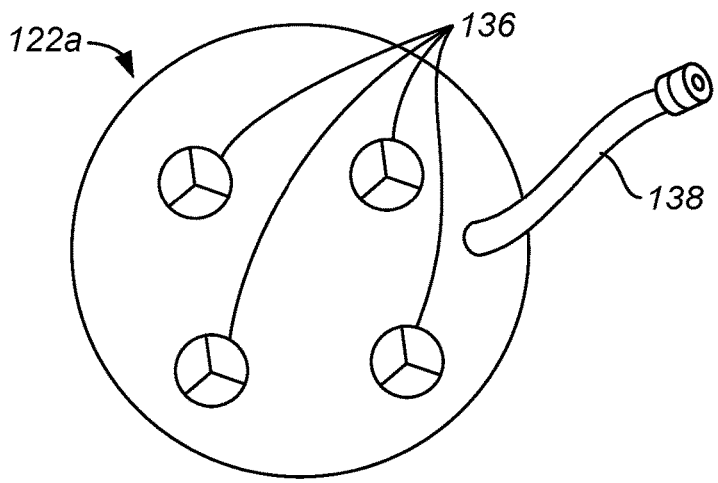
FIGS. 8A, 8B, and 8C are alternative top views of the exemplary access port seal of FIG. 6.
Figure 8B:
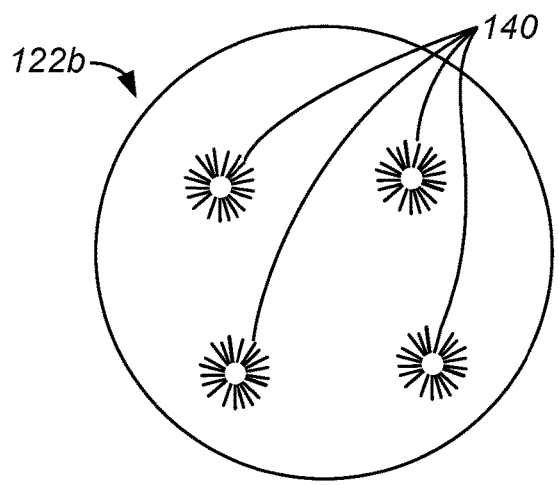
Figure 8C:
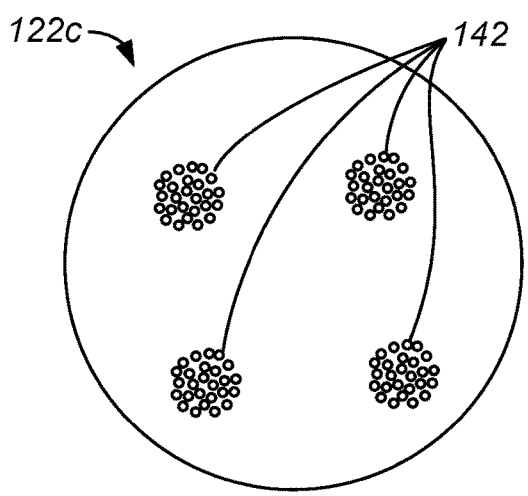

As shown in FIGS. 8A through 8C, in some instances, the upper openings of the tool passing channels may be covered with conventional valve covers 136 FIG. 8A), such as split membrane valve covers, which allow tools to be passed there through but which close to form a seal when no tool is present through the slits.

Additionally or alternatively, the tool passing channels 130 may further comprise a plurality of reinforcement tracks 140 (FIG. 8B) which serve to facilitate passage of laparoscopic tools through the tool passing channels. The tracks 140 will act both to protect the integrity of the tool passing channel 130' (FIG. 7A) as the tools are introduced and also to guide and facilitate passage of the tools through the channels.

Similarly, as shown in FIG. 8C, the built tool channels may be protected by a matrix or distribution of small reinforcement pads, such as polymeric dots or beads 142 which are formed over the entire length of the tool passing channel.

In all cases, the tool passing channels may be lubricated to further assist passage of tools, scopes, and the like therethrough.

Figure 9A:
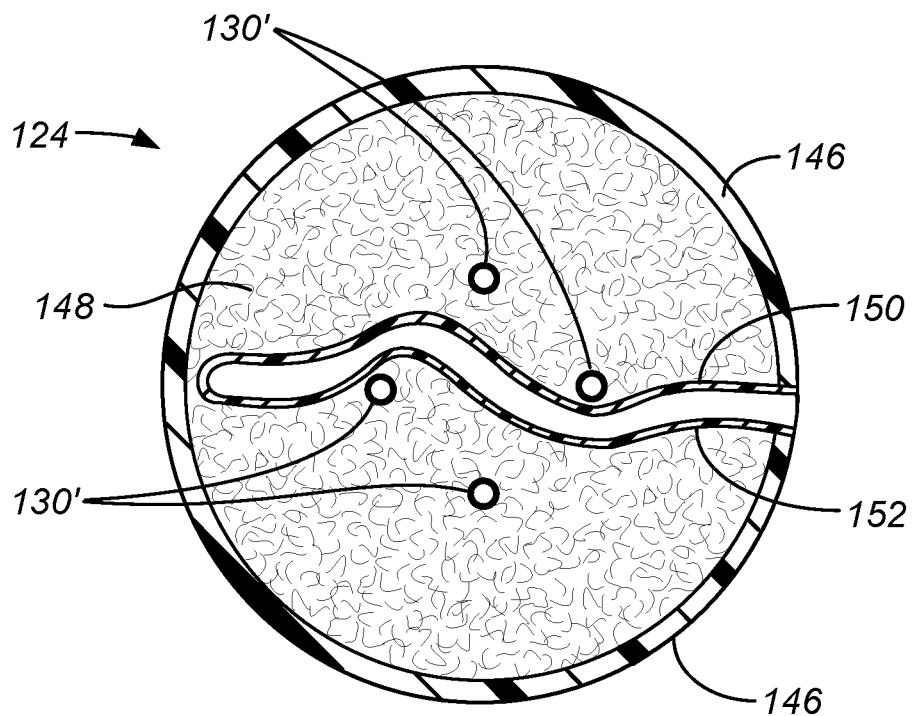
FIGS. 9A and 9B are sectional views through a neck region of the exemplary access port seal of FIG. 6 showing an insertion channel in a serpentine configuration (FIG. 9A) and in a straightened configuration having an insertion tool therein (FIG. 9B).
Figure 9B:
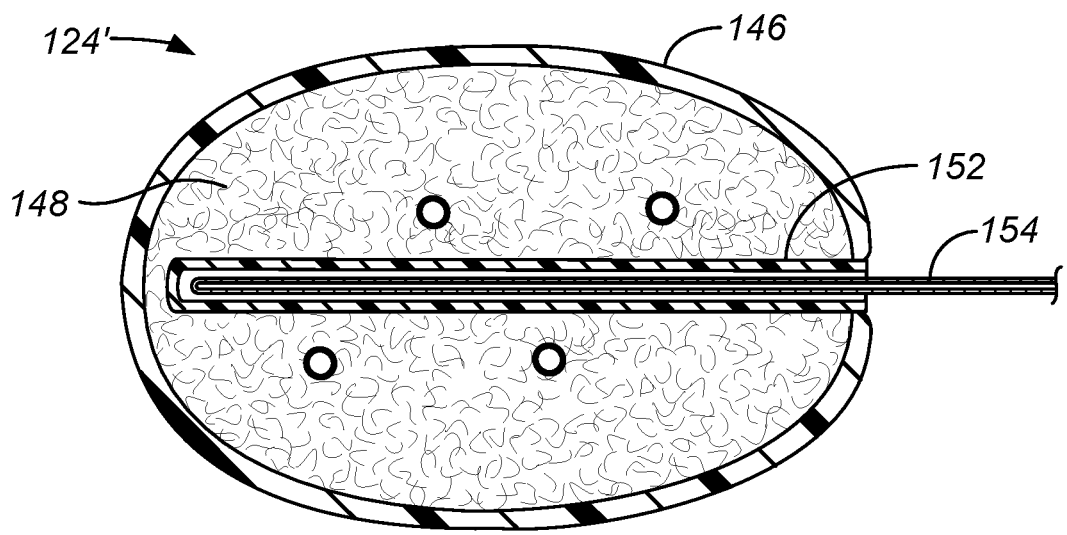

Referring now to FIGS. 9A and 9B, in order to facilitate introduction of the deformable body through an aperture in a laparoscopic port, an insertion channel 150 may be formed laterally across the lower region 124 of the body. In specific embodiments, the deformable body will comprise an outer shell 146 which typically comprise an elastic, semi-elastic, or in some cases non-distensible polymeric material on membrane. The outer shell may consist of a single material or may comprise two or mare materials, wherein such multiple materials may be laminated, heat welded, adhesively bonded, or otherwise formed in a single, contiguous shell with an interior that is filled with a filler Material 148.

The filler material 148 is disposed in the interior of the outer shell and will comprise a flowable filler material, such as a hydrogel, viscous liquid, beads, air and other gasses, or the like. In all cases, the filler material will allow deformation of the deformable seal as it is introduced through the aperture of the laparoscopic port and also as laparoscopic tools are passed through the tool passing channels.

In preferred instances, the insertion channel 150 will have a curved or serpentine shape on the deformable seal is not deformed, as shown in FIG. 9A. In this way, an insertion tool, typically having a straight shaft 154, can be introduced through the insertion channel 150 in order to straighten the channel and elongate the lower region 124 of the seal body 120. Such elongation facilitates introduction of the lower portion through an aperture of a port as described in more detail below. Preferably, the insertion channel 150 will be protected by an insertion sheath 152 which is sufficiently flexible to allow straightening and which is sufficiently strong to prevent damage to the deformable body as the insertion tool is being introduced.

Figure 10A:
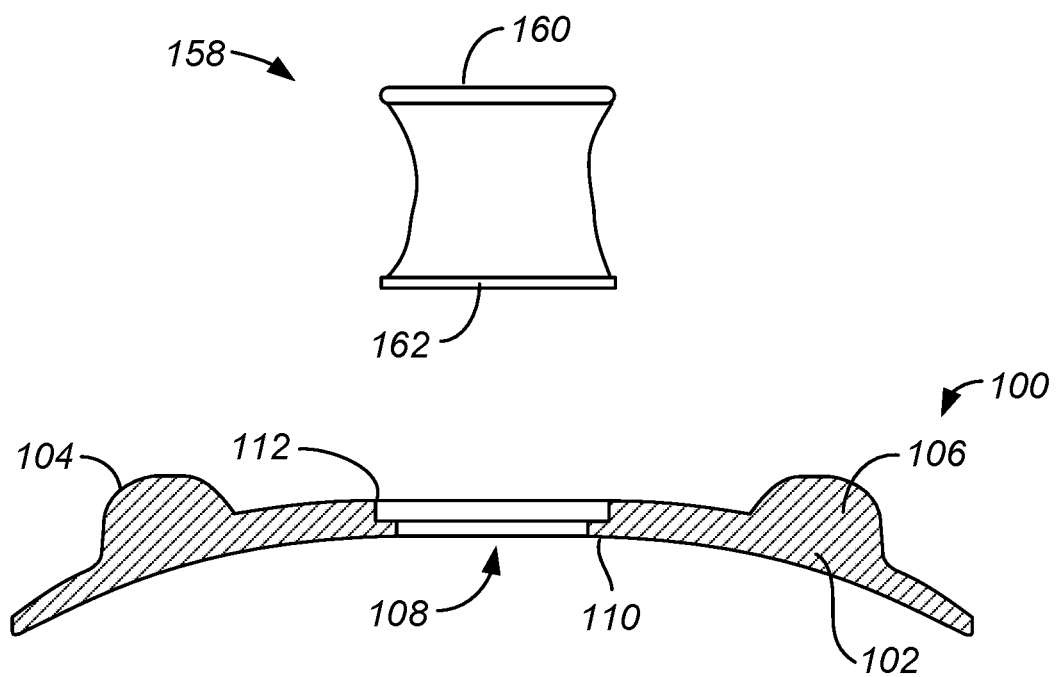
FIGS. 10A through 10F illustrate the insertion and removal of the access port seal of FIG. 6 through the laparoscopic access port of FIG. 4.
Figure 10B:
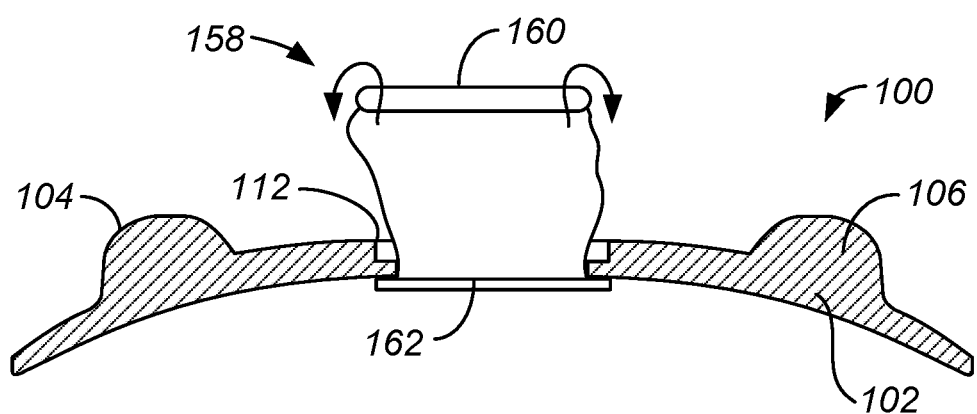

Referring now to FIGS. 10A through 10F, methods of the present invention for introducing the deformable seal 120 into the laparoscopic port 100 will be described. As shown in FIG. 10A, the laparoscopic port 100 may be placed over a patient's stomach (not shown) with the aperture 108 aligned over the patient's umbilicus. After opening the umbilicus with an incision, a transcutaneous seal 158 is introduced through the aperture 108 and the lower end of the sleeve inserted into the patient's abdomen, as shown in FIG. 10B, typically manually. Note for simplicity, the abdominal wall is not shown, but it should be appreciated that a lower ring 162 of the seal will be introduced through both the port 108 and the incision so that the ring engages an internal surface of the abdominal wall. Typically the ring will be itself deformable so that it can be squeezed to be placed through the incision allowed to expand into engagement with the internal wall.

Figure 10C:
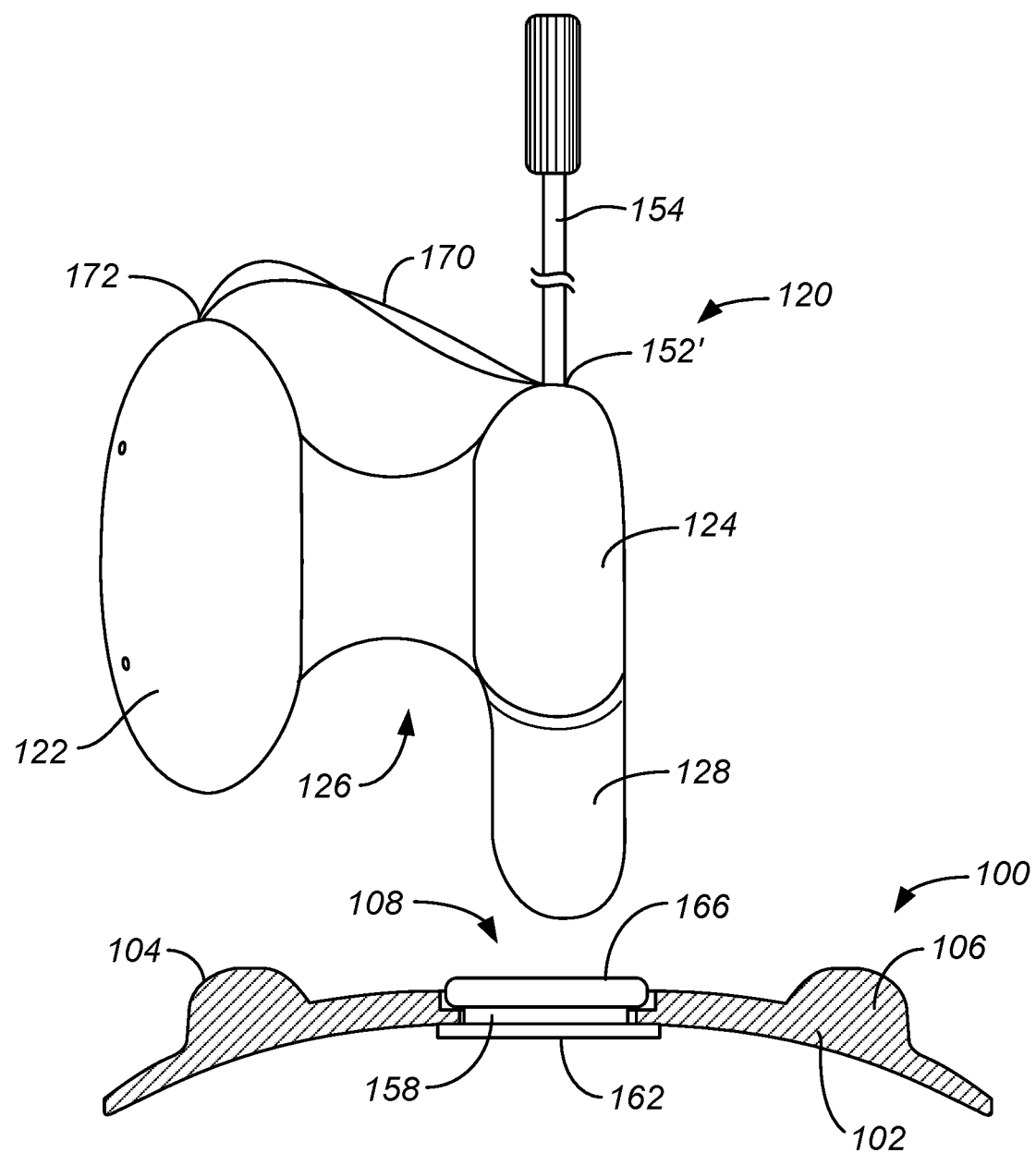

After the transcutaneous sleeve 158 has been introduced, an upper ring 160 will be rolled downwardly, as shown by the arrows in FIG. 10B, until a rolled top 166 engages an upper surface of the flange 110, as shown in FIG. 10C. In this way, the laparoscopic port will be anchored on the patient's stomach and the aperture fixedly aligned with the incision through the umbilicus.

Figure 10D:
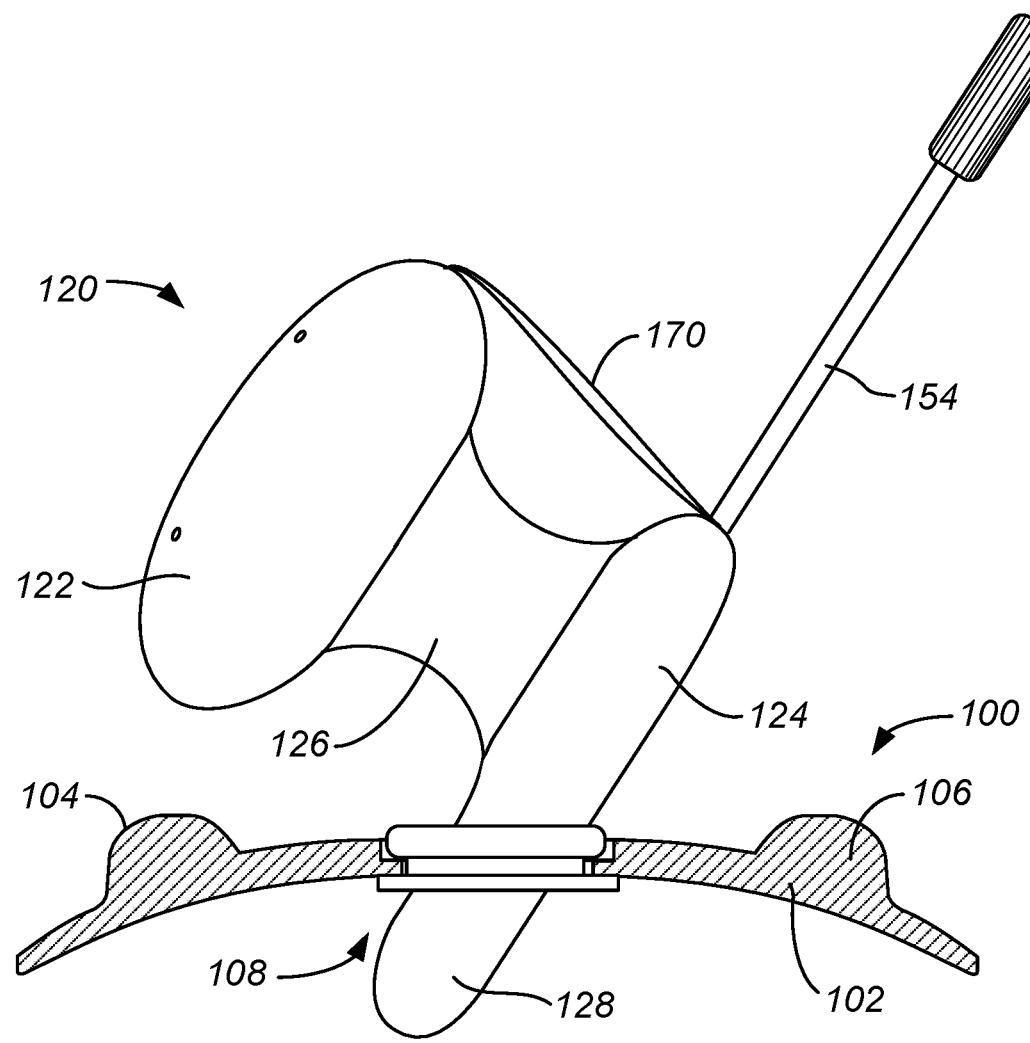
Figure 10E:
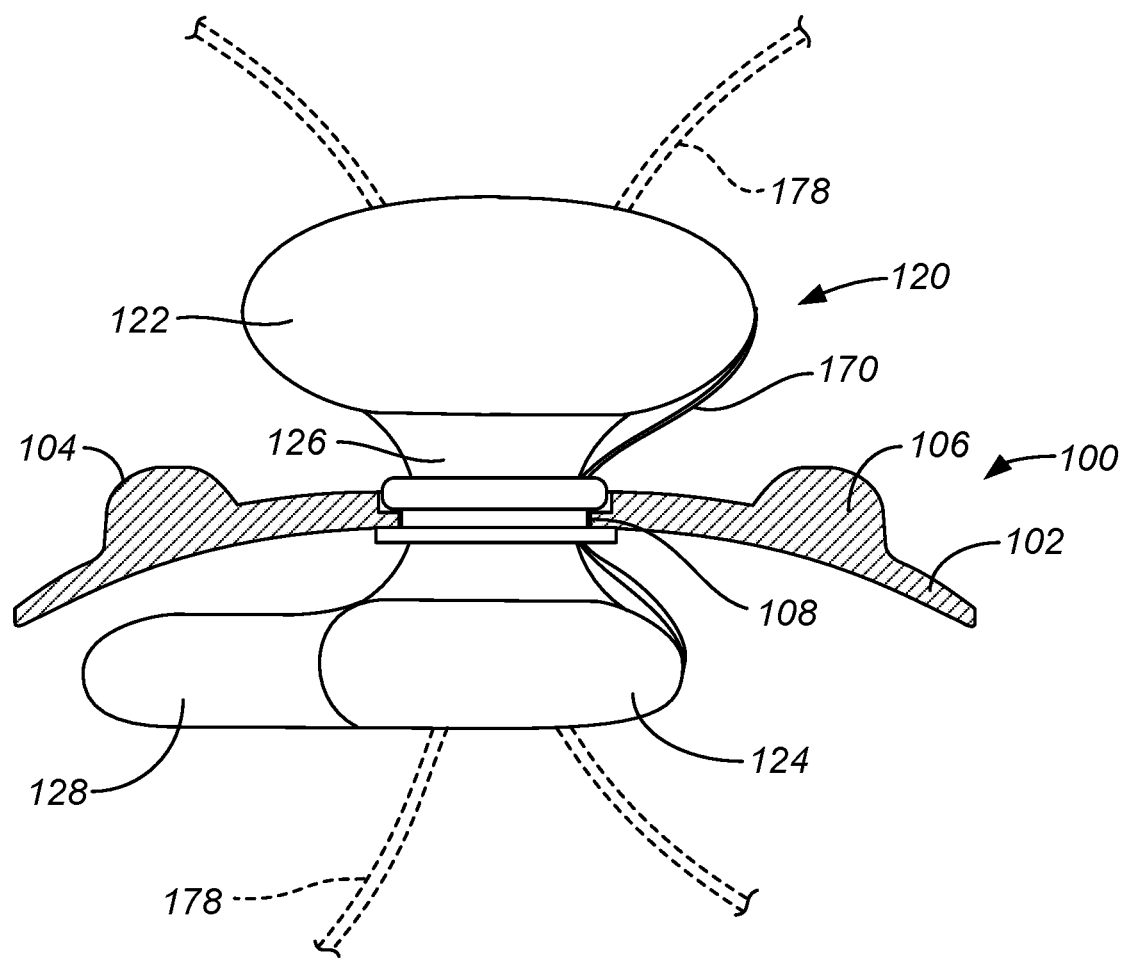

Once the laparoscopic port 100 has been anchored in place, as shown in FIG. 10C, the deformable seal 120 will be positioned so that nose 128 is aligned with the aperture 108 of the laparoscopic port. Shaft 154 of the insertion tool is placed in the insertion channel 150, and the insertion tool advanced in order to straighten the insertion channel 150 and reduce the profile of the nose 128 and lower region 124, as shown in FIG. 9B above. The nose 128 can then be introduced through the aperture 108, as shown in FIG. 10D, and further advanced until the lower region 124 is fully through the aperture and located in the patient's abdominal cavity, as shown in FIG. 10E. The insertion tool is then removed, and the lower region 124 self-expands into its unconstrained configuration with the narrowed waist 126 located within the interior of the aperture engaging a periphery of the transcutaneous sleeve 158.

Tools 128, shown in broken line in FIG. 10E, can then be introduced and attached to the arms of 52 of the laparoscopic port 100, as shown in FIGS. 4 and 5. The tools are generally manipulated as described in prior U.S. Patent Publications 2012/0116362 and 2016/0081752, the full disclosures of which have been previously incorporated herein and by reference.

Figure 10F:
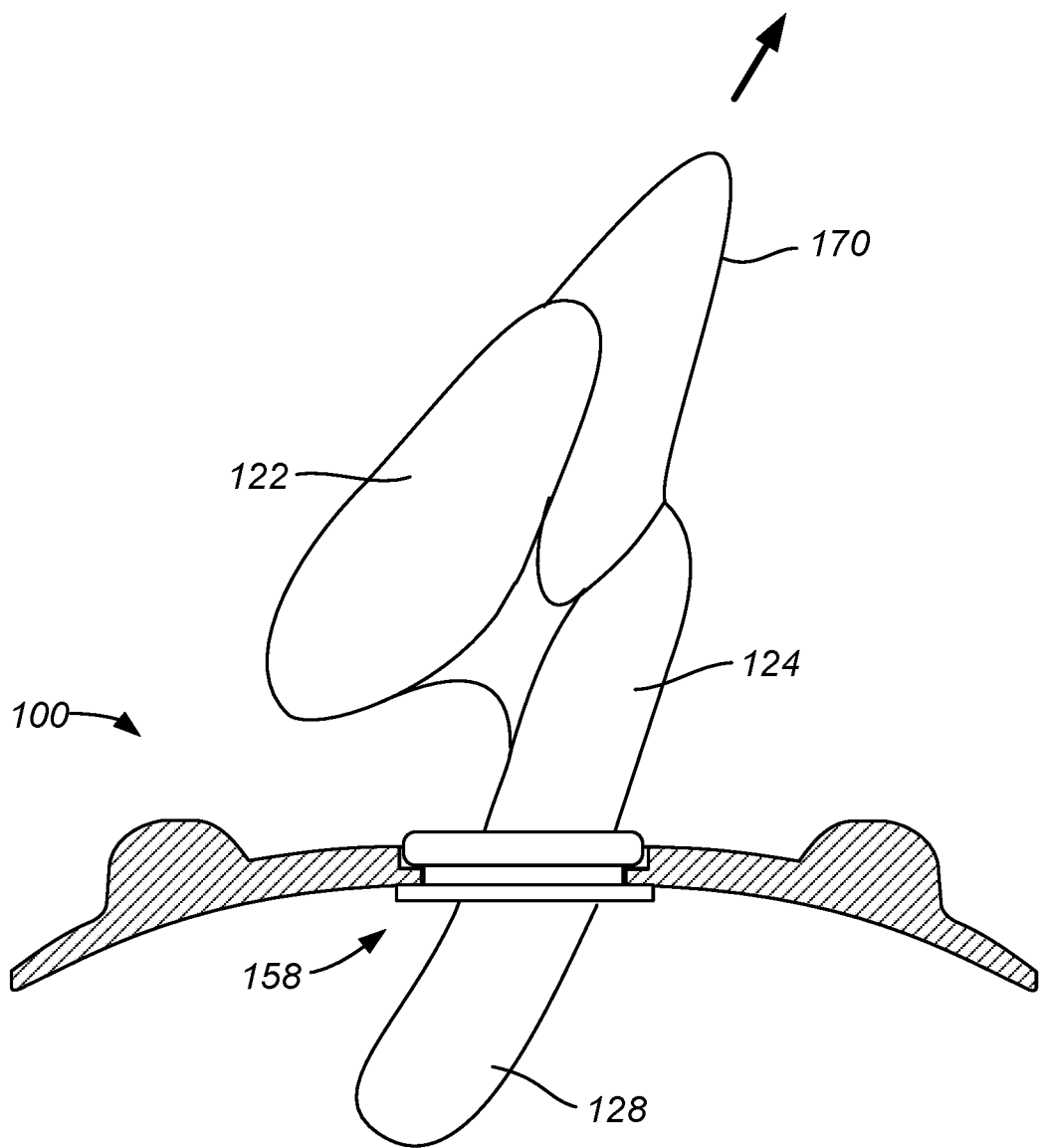

After the laparoscopic procedure has been completed, the deformable body 120 may be removed by pulling upwardly on the pull strap 170, as shown in FIG. 10F, in order to remove the seal from the aperture. Once the deformable seal has been removed, the transcutaneous sleeve can be unrolled releasing the laparoscopic port 100 from the patient, and the incision can be closed in the conventional manner.

All references, including publications, patent applications, and patents, cited herein are hereby incorporated by reference to the same extent as if each reference were individually and specifically indicated to be incorporated by reference and were set forth in its entirety herein.

The foregoing examples are not intended to limit the scope of the invention. All modifications, equivalents and alternatives are within the scope of the invention.

What is claimed is:

1. A method for performing laparoscopic surgery through a single port, said method comprising:
    securing a frame having a central opening defining an aperture over an incision in a patient's abdomen to define the single port;
    introducing a deformable seal into and through the aperture, wherein a lower region of the deformable seal passes through the aperture and into a patients abdominal cavity and an upper region of the deformable seal remains above the aperture with a narrowed waist between the upper and lower regions secured in a perimeter of the aperture, wherein introducing the deformable seal through the aperture comprises inserting an introducing tool into a channel formed laterally across the lower region of the deformable seal and manually advancing the introducing tool to push and deform the lower region of the deformable seal so that said lower region can pass through the aperture and self-expand on the other side of the single port with the narrowed waist in the aperture;
    introducing a first laparoscopic tool through a first tool passing channel in the deformable seal so that the first tool passing channel conforms to and seals against a shaft of the first laparoscopic tool;
    introducing a second laparoscopic tool through a second tool passing channel in the deformable seal so that the second tool passing channel conforms to and seals against a shaft of the second laparoscopic tool.

2. A method as in claim 1, wherein the upper region is larger than the lower region and the lower region is deformed to pass through the aperture in the frame and allow the narrowed waist to seat in the aperture and to seal to the aperture.

3. A method as in claim 1, wherein at least one of the first and second tool passing channels has an arcuate shape configured to receive a laparoscopic tool having an arcuate midsection.

4. A method as in claim 3, further comprising introducing the first and second laparoscopic tools through valves formed over respective entrances of the first tool passing channel and the second tool passing channel on an upper surface of the upper region of the deformable seal.

5. A method as in claim 1, wherein the introducing tool comprises a shaft.

6. A method as in claim 1, further comprising removing the deformable seal from the aperture by pulling on a pull strap affixed to the lower region.

7. A method as in claim 1, wherein the deformable seal comprises flexible shell filled with a filler material that will shift location within the flexible shell in response to external forces externally on the flexible shell and/or internally within the tool passing channels.

8. A method as in claim 7, wherein the flexible shell comprises a polymeric membrane and the filler material comprises a gel.

9. A method as in claim 1, further comprising insufflating the patient's abdominal cavity with gas via a gas channel embedded within the deformable seal.

10. A method as in claim 1, further comprising:
    attaching the first laparoscopic tool to a first pivotal attachment element on a first location on an outer periphery of the frame;
    attaching the second laparoscopic tool to a second pivotal attachment element at a second location on the outer periphery of the frame;
    wherein each laparoscopic tool has distal and proximal sections which lie on axes passing through the pivotal attachment elements and mid-portions which remain positioned within the central opening of the frame but avoid interference as the tools are manipulated by a user during a surgery.

11. A method as in claim 10, further comprising detaching one of the first and second laparoscopic tools and attaching a third tool to the respective pivotal attachment element, wherein the third tool has distal and proximal sections which lie on an axis passing through the pivotal attachment element and a mid-portion which remains positioned within the central opening of the frame as the tools are manipulated by the user during the surgery.

12. A method as in claim 10, further comprising manipulating the proximal sections of the tools to pivotally position the distal sections at desired locations within a surgical field.

13. A method as in claim 12, further comprising axially extending and retracting the proximal sections of the tools to axially extend and retract the distal sections.

\* \* \* \* \*